United States Patent
Vachon et al.

(10) Patent No.: US 11,174,439 B2
(45) Date of Patent: Nov. 16, 2021

(54) METHOD TO INHIBIT POLYMERIZATION IN A PROCESS WATER

(71) Applicants: Ecolab USA, Inc., St. Paul, MN (US); SABIC Global Technologies B.V., Bergen op Zoom (NL)

(72) Inventors: Jerome Vachon, Maastricht (NL); Anthoni van Zijl, Eindhoven (NL); Fabrice Cuoq, Beverwijk (NL); Steven Leen, Bree (BE); Carlo Geijselaers, Eindhoven (NL); Andrew R. Neilson, Richmond, TX (US); Russell P Watson, Idaho Falls, ID (US)

(73) Assignee: Ecolab USA Inc., St. Paul, MN (US)

( * ) Notice: Subject to any disclaimer, the term of this patent is extended or adjusted under 35 U.S.C. 154(b) by 301 days.

(21) Appl. No.: 16/326,035

(22) PCT Filed: Aug. 23, 2017

(86) PCT No.: PCT/US2017/048151
§ 371 (c)(1),
(2) Date: Feb. 15, 2019

(87) PCT Pub. No.: WO2018/044644
PCT Pub. Date: Mar. 8, 2018

(65) Prior Publication Data
US 2019/0185761 A1    Jun. 20, 2019

Related U.S. Application Data

(60) Provisional application No. 62/381,984, filed on Aug. 31, 2016.

(51) Int. Cl.
*C10G 9/16* (2006.01)
*C09K 8/524* (2006.01)
(Continued)

(52) U.S. Cl.
CPC .................. *C10G 9/16* (2013.01); *C02F 1/68* (2013.01); *C07C 4/04* (2013.01); *C09K 8/524* (2013.01);
(Continued)

(58) Field of Classification Search
None
See application file for complete search history.

(56) References Cited

U.S. PATENT DOCUMENTS

| 5,711,767 A | 1/1998 | Gande et al. |
| 6,835,288 B1 | 12/2004 | Sutoris et al. |

(Continued)

FOREIGN PATENT DOCUMENTS

| CN | 1172149 A | 2/1998 |
| CN | 101838058 A | 9/2010 |

(Continued)

OTHER PUBLICATIONS

Office Action in Chinese Application No. 201780049666.8, dated Dec. 10, 2020, 17 pages (9 pages English Translation & 8 pages Official Copy).

(Continued)

*Primary Examiner* — Clare M Perrin
(74) *Attorney, Agent, or Firm* — Kagan Binder, PLLC (57) ABSTRACT

Disclosed herein are methods for reducing fouling caused by process water present within a water recycling loop of a pyrolysis plant. Fouling is caused by phase separation and accumulation of materials from the process water on equipment surfaces. The method includes applying a total of about 5 ppm to 500 ppm total of a first polymerization inhibitor and second polymerization inhibitor to the process water to form a treated process water, wherein the first polymerization inhibitor has a pygas-water partition coefficient of about (Continued)

0.0001 to 9 and the second polymerization inhibitor has a pygas-water partition coefficient of about 1000 to 50,000.

10 Claims, 1 Drawing Sheet

(51) Int. Cl.
    *C07C 4/04*         (2006.01)
    *C23F 14/02*       (2006.01)
    *C02F 1/68*         (2006.01)
    *C10G 75/04*       (2006.01)
    *C23F 15/00*       (2006.01)
    *C02F 101/32*      (2006.01)
    *C02F 103/36*      (2006.01)

(52) U.S. Cl.
    CPC .............. *C10G 75/04* (2013.01); *C23F 14/02* (2013.01); *C23F 15/005* (2013.01); *C02F 2101/32* (2013.01); *C02F 2103/365* (2013.01); *C10G 2300/1092* (2013.01); *C10G 2300/4075* (2013.01); *C10G 2300/80* (2013.01); *C10G 2400/20* (2013.01)

(56) References Cited

U.S. PATENT DOCUMENTS

| | | | |
|---|---|---|---|
| 2005/0263437 A1* | 12/2005 | Howdeshell | C10G 75/04 208/48 AA |
| 2010/0314239 A1* | 12/2010 | Gropp | C07C 51/06 203/35 |
| 2012/0203020 A1 | 8/2012 | Tong | |

FOREIGN PATENT DOCUMENTS

| | | | | |
|---|---|---|---|---|
| EP | 1897908 A1 | * | 3/2008 | ............. C10B 43/14 |
| EP | 1897908 A1 | | 3/2008 | |
| JP | H 03-086792 A | | 4/1991 | |
| WO | WO01047844 A1 | * | 5/2001 | |
| WO | 01/47844 A1 | | 7/2001 | |
| WO | WO-2015055843 A1 | * | 4/2015 | ......... B01D 11/0446 |

OTHER PUBLICATIONS

International Search Report for Application No. PCT/US2017/048151, dated Nov. 3, 2017, 5 pages.
Written Opinion for Application No. PCT/US2017/048151, dated Nov. 3, 2017, 7 pages.
Examination Report mailed in Indonesian Application No. PID201901512, dated Oct. 26, 2020, 5 pages (3 pages Official Copy & 2 pages English Translation).
Examination Report mailed in GCC Application No. GC 2017-33906, dated Apr. 7, 2019, 5 pages.
Office Action mailed in European Application No. 17764700.5, dated Dec. 19, 2020, 7 pages.
Examination Report mailed in GCC Application No. GC 2017-33906, dated Feb. 24, 2020, 4 pages.
Office Action in Japanese Patent Application No. 2019-511496, dated Sep. 7, 2021, 6 pages (3 pages English Translation & 3 pages Official Copy).

* cited by examiner

METHOD TO INHIBIT POLYMERIZATION IN A PROCESS WATER

CROSS-REFERENCE TO RELATED APPLICATIONS

This application claims priority to International Application No. PCT/US2017/048151, filed Aug. 23, 2017, and titled "METHOD TO INHIBIT POLYMERIZATION IN A PROCESS WATER", which in turn claims priority from U.S. Provisional Application having Ser. No. 62/381,984, filed on Aug. 31, 2016, both of which are incorporated herein by reference in their entireties.

TECHNICAL FIELD

The invention is directed to polymerization inhibitors and methods of using the polymerization inhibitors in one or more industrial pyrolysis operations.

BACKGROUND

In the production of petrochemicals, water is often used to control various chemical reactions, for example by transferring heat from process streams to quench reactions. When such water is subjected to intimate contact with a process stream, it is commonly referred to as process water. In ethylene manufacturing plants, steam is contacted with the process feedstock to control the pyrolysis (cracking) process by lowering the partial pressure of the hydrocarbon feedstock, improving the efficiency of the conversion reaction. Downstream of the pyrolysis reactors, a water quench tower is further employed to cool the gas leaving a primary fractionator or a transfer line exchanger.

In pyrolysis processes including ethylene production processes, the Dilution Steam System (DSS) typically consists of a series of fluidly connected devices including one or more of a quench water tower, an oil/water separator, a process water stripper, and a dilution steam generator, in various combinations and in some cases including two more of such devices. Collectively, the DSS devices in fluid connection represent a water recycling loop. Steam from the dilution steam generator is sent to the pyrolysis furnace and is recovered as water in the quench water tower. Temperatures at the base of the quench water tower can approach 100° C., for example about 60° C. to 100° C., or about 80° C. to 90° C.

The water recycling loop can experience a variety of problems due to conditions and compounds present in the quench water tower. Significant quantities of pygas, pytar, and various other contaminants formed as a result of the pyrolysis process can concentrate in the process water of the quench water tower. If unchecked, these contaminants can lead to fouling of equipment, that is, deposition on interior surfaces of the dilution steam system. Lack of effective gasoline/water separation in a quench water tower (QWT) or quench water settler (QWS) leads to pygas, pytar, and reacted or reactive byproducts of these circulating through the DSS. Fouling potential is due to the presence of reactive species such as polymerizable compounds originating in the pygas or pygas-pytar, heat removal by "pumparounds," and a mixture of hydrogen, steam, and generally harsh conditions present during operation of the water recycling loop. For example, in some cases these contaminants or reacted byproducts thereof accumulate on heat exchange surfaces or even proceed into the boiler, where it must be separated from the recyclable water and disposed of as "blowdown." In some embodiments, as much as 5%-10% of total water volume in the system is blown down. Since blowdown water is also employed to preheat incoming water within the recycling loop, the blowdown water is cooled and this in turn can result in additional precipitation and accumulation of polymerized solids on device surfaces.

Byproducts associated with fouling include oligomers and polymers including the polymerized residues of one or more styrenes, indene, isoprene, and the like, as well as co-oligomers and co-polymers incorporating residues of a variety of other polymerizable compounds present in pygas. Capturing styrene and other polymerizable compounds in the quench tower recycling loop exacerbates fouling by providing conditions that lead to polymerization, causing deposition of polymerized products on equipment surfaces.

The pygas emulsions with process water are distinct and different from those that are found in oil field produced water. Oil field produced waters contain species almost never found in the subject quench waters. Thus, emulsions present in the process water are distinct from those found in oil field produced water. The process water emulsions are subjected to a different set of conditions than those of oil field produced water as well; the combined effect of these difference is that solutions for addressing emulsions in oil field produced waters are not generally effective for resolving fouling problems in quench tower recycling loops.

Due to the presence of pygas within a quench water tower (QWT) or quench water settler (QWS) of such pyrolysis plants, coupled with harsh conditions including high temperatures, polymerized products form and can subsequently be carried along with the process water to the process water stripper (PWS). By way of example, capturing styrene in the quench water tower exacerbates fouling by providing conditions favorable for its polymerization, leading eventually to deposition of the styrenic products on equipment surfaces. This causes fouling not only at the bottom of the PWS, but also at the dilution steam generator (DSG) preheaters. This in turn leads to poor energy efficiency and in worse cases, to plant shutdowns due to cumulative fouling. The DSG also fouls due to byproduct carry-over, and the QWT may suffer fouling as well. For plants employing feed saturators in lieu of dilution steam generators, analogous fouling and deleterious results also occur.

Thus, there is a need in the industry to reduce fouling within the dilution steam systems of ethylene-producing or other pyrolysis plants. Less fouling improves the energy efficiency of the system, prevents plant throughput reduction, and prevents product quality issues in the process water due to the use of recycled process water as quench water.

SUMMARY

Disclosed herein is a method of reducing fouling caused by process water comprising water and a pygas present within a water recycling loop of an industrial process, the method comprising applying a combined total of about 5 ppm to 500 ppm by weight of first and second polymerization inhibitors to the process water to form a treated process water, wherein the first polymerization inhibitor has a pygas:water partition coefficient of greater than zero but less than 9, and the second polymerization inhibitor has a pygas:water partition coefficient of between about 1000 and 50,000. In embodiments, the first and second polymerization inhibitors are added to a process water within a water recycling loop of an industrial process at a weight ratio of about 1:9 to 9:1.

In some embodiments, the industrial process is pyrolysis, and the water recycling loop is present within a pyrolysis plant. In some embodiments, the applying is downstream from a coalescer in the pyrolysis plant. In some embodiments, the applying is carried out continuously. In some embodiments, during the applying the process water is present at a temperature of about 60° C. to 100° C.

Also disclosed herein is a composition comprising a process water, a first polymerization inhibitor, and a second polymerization inhibitor, wherein the first polymerization inhibitor has a pygas:water partition coefficient of greater than zero but less than 9, and the second polymerization inhibitor has a pygas:water partition coefficient of between about 1000 and 50,000.

Additional advantages and novel features of the invention will be set forth in part in the description that follows, and in part will become apparent to those skilled in the art upon examination of the following, or may be learned through routine experimentation upon practice of the invention.

DETAILED DESCRIPTION

Although the present disclosure provides references to preferred embodiments, persons skilled in the art will recognize that changes may be made in form and detail without departing from the spirit and scope of the invention. Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Definitions

As used herein, "water recycling loop" means a series of fluidly connected devices including one or more of a quench water tower, an oil/water separator, a process water stripper, and a dilution steam generator, in various combinations and in various order relative to each other within the fluid connection, and in some cases including two or more of such devices. In embodiments, during operation of the fluidly connected devices, steam from a dilution steam generator is sent to a pyrolysis furnace and is recovered as liquid in the quench tower. In such embodiments, temperatures at the base of the quench water tower can approach 100° C., for example about 60° C. to 100° C., or about 80° C. to 90° C.

As used herein, the term "process water" means water plus one or more pyrolysis byproducts present within a water recycling loop. In some embodiments, the process water includes pygas, pygas byproducts, or a mixture thereof. Temperature of the process water in at least one portion of the water recycling loop is about 60° C. to 100° C., or about 80° C. to 90° C.

As used herein, the term "pyrolysis byproduct" means pygas, pytar, another material, or combination of two or more thereof formed as a byproduct of a pyrolysis procedure.

As used herein, the term "pygas" is a term of art and shorthand for "pyrolysis gasoline." Pygas is a pyrolysis byproduct that is less dense than water and is a mixture of petroleum based products that condenses along with water in the quench water tower of a dilution steam system of an industrial processing plant, such as a pyrolysis plant. Pygas is a variable mixture of hydrocarbons and other byproducts, wherein the mixture components and amounts are determined by the feedstock and conditions employed in the pyrolysis. As determined by context and/or unless otherwise specified, pygas includes one or more aromatic compounds and a mixture of alkanes and alkenes having at least 5 carbons, wherein a majority (i.e., more than 50 wt %) of the alkane/alkene component is $C_5$-$C_{12}$. In some embodiments, pygas is rich in benzene (for example, 20 wt %-45 wt %). Pygas also contains highly reactive olefins and diolefins such as styrene, isoprene, piperylenes, cyclopentadienes, and combinations thereof. In some embodiments, pygas further includes components such as $C_1$-$C_5$ organic acids. In some embodiments, pygas includes about 0.01 wt % to as much as about 20 wt % pytar based on the total weight of a pygas-pytar mixture, where the amount of pytar depends on the individual equipment employed for cracking and the feedstock. Unless otherwise specified, or in context, "pygas" includes both pygas and mixtures thereof with pytar, pygas byproduct, or both. "Pygas byproduct" means any one or more compounds formed as the product of a chemical reaction of one or more components of pygas (including pygas-pytar mixtures) wherein the reaction takes place within a dilution steam system of a pyrolysis plant, further wherein the reaction results in an increase in molecular weight of one or more of the reacted components. In some embodiments, a pygas byproduct includes an oligomerized or polymerized residue of styrene and/or one or more unsaturated and radically polymerizable components of the pygas.

As used herein, the term "fouling" means phase separation of pygas components or pygas byproducts from a process water. In some embodiments, fouling is further coupled with measurable accumulation of pygas components or pygas byproducts on one or more solid interior surfaces of a device, wherein the device is disposed in fluid connection within a dilution steam system. "Measurable" in this context means the accumulation is visible or quantifiable by weighing or using one or more analytical methods. "Interior" in this context means a solid surface in fluid contact with at least a process water during operation of a water recycling loop of an industrial processing plant.

As used herein, the term "polymerization inhibitor" means a compound capable of inhibiting a polymerization reaction of one or more radically polymerizable species.

As used herein, the chemical names of polymerizable species (e.g., styrene, acrylic acid) are used to mean either the chemical species itself or a polymerized residue thereof in one or more oligomers or polymers, as determined by context.

As used herein, the term "optional" or "optionally" means that the subsequently described event or circumstance may but need not occur, and that the description includes instances where the event or circumstance occurs and instances in which it does not.

As used herein, the term "about" modifying, for example, the quantity of an ingredient in a composition, concentration, volume, process temperature, process time, yield, flow rate, pressure, and like values, and ranges thereof employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe any range of values, for example "about 1 to 5" the recitation means "1 to 5" and "about 1 to about 5" and "1 to about 5" and "about 1 to 5" unless specifically limited by context.

As used herein, the word "substantially" modifying, for example, the type or quantity of an ingredient in a composition, a property, a measurable quantity, a method, a position, a value, or a range, employed in describing the embodiments of the disclosure, refers to a variation that does not affect the overall recited composition, property, quantity, method, position, value, or range thereof in a manner that negates an intended composition, property, quantity, method, position, value, or range. Examples of intended properties include, solely by way of nonlimiting examples thereof, partition coefficient, rate, solubility, temperature, and the like; intended values include yield, weight, concentration, and the like. The effect on methods that are modified by "substantially" include the effects caused by variations in type or amount of materials used in a process, variability in machine settings, the effects of ambient conditions on a process, and the like wherein the manner or degree of the effect does not negate one or more intended properties or results; and like proximate considerations. Where modified by the term "substantially" the claims appended hereto include equivalents to these types and amounts of materials.

Discussion

Disclosed herein are methods of preventing or reducing fouling within a water recycling loop of an industrial processing system. In some embodiments, the water recycling loop is provided by operation of a dilution steam system within a pyrolysis plant. The methods include applying a first polymerization inhibitor and a second polymerization inhibitor to a water recycling loop, wherein the first polymerization inhibitor has a pygas-water partition coefficient of greater than zero and less than 9 and the second polymerization inhibitor has a pygas-water partition coefficient of greater than 1000 and as much as 50,000. The methods are effective to reduce or prevent fouling within the water recycling loop.

Also disclosed herein is a method of inhibiting polymerization in a pygas-water emulsion, the method comprising applying a first polymerization inhibitor and a second polymerization inhibitor to a process water to form a treated process water, wherein the first inhibitor has a pygas-water partition coefficient of greater than zero and less than 9 and the second inhibitor has a pygas-water partition coefficient of greater than 1000 and as much as 50,000; and contacting the treated process water with an interior surface within the water recycling loop. The methods are effective to reduce or prevent fouling of the contacted surfaces.

In some embodiments, the first and second polymerization inhibitors are applied to a device disposed in fluid connection within a water recycling loop, wherein the device comprises, consists essentially of, or consists of a quench water tower (QWT), a quench water settler (QWS), a process water stripper (PWS), a dilution steam generator (DSG), a feed saturator (FS), or two or more thereof. Each such device is fluidly connected to one or more other devices in a manner that facilitates recycling of the water within the water recycling loop. Where such devices are present as part of the water recycling loop of a pyrolysis plant, each such device is fluidly contacted within the interior thereof by one or more mixtures of process water (including process water treated according to the methods disclosed herein), pygas, and pygas byproducts.

In some embodiments, the processing system is a pyrolysis plant. In some embodiments, the pyrolysis plant is an ethylene manufacturing plant. In some embodiments, the feedstock of an ethylene manufacturing plant comprises, consists essentially of, or consists of naphtha, ethane, propane, butane, or a combination thereof.

According to the methods of the invention, a combined total of about 5 ppm to 500 ppm by weight of first and second polymerization inhibitors are applied to a water recycling loop of an industrial processing system, such as an ethylene manufacturing plant or "cracker." In some embodiments, a solution or dispersion of the first and second polymerization inhibitors is formed initially, then the solution or dispersion is applied to process water present within a device disposed in fluid connection within the water recycling loop. The presence of the first and second polymerization inhibitors in the treated process water prevents or reduces the amount of fouling of surfaces contacting the treated process water within the water recycling loop.

The process water includes at least pygas and water. These two materials, including additional compounds dissolved in one or both thereof, are generally immiscible. For example, styrene, a polymerizable liquid compound commonly present in pygas, is known to be immiscible with water. Thus, at least two phases exist within the process water of a water recycling loop: a pygas phase and a water phase. As stated above, it is further known that pygas and associated compounds present in water recycling loops form emulsions. Such emulsions include a pygas phase that is a hydrophobic phase, and an aqueous phase including the water added as part of the steam dilution process. In some embodiments, one or more types of emulsions exist in at least one portion of a water recycling loop. The polymerizable compounds present in the process water, such as styrene, tend to strongly partition to the pygas phase: that is, most or substantially all of any one such compound present in a process water (emulsified or not) should reside within the pygas phase of the process water.

Since most if not substantially all polymerizable compounds present in a process water are expected to partition strongly to the pygas phase, it is unexpected that a mixture of two chemically distinct polymerization inhibitors, one partitioning strongly to the water phase and one partitioning strongly to the pygas phase, are effective in reducing fouling within a water recycling loop. We have found that application of about 5 ppm to 500 ppm of a combination of first and second polymerization inhibitors is more effective than the use of the same amount by weight of the second polymerization inhibitor alone at preventing fouling within a water recycling loop.

Polymerization Inhibitors.

Effective inhibition of polymerization and concomitant fouling is achieved in a process water loop by applying to the process water loop two chemically distinct polymerization inhibitors, wherein a first polymerization inhibitor has a pygas-water partition coefficient of greater than zero and less than 9, and a second polymerization inhibitor has a pygas-water partition coefficient of greater than 1000 and as much as 50,000. The first and second polymerization inhibitors are both compounds that are capable of inhibiting polymerization of radically polymerizable species.

Pygas-water partition coefficients are determined by measuring the concentration of a polymerization inhibitor in a pygas-water mixture. In some embodiments, a pygas from an actual process water sample is used as the pygas in the determination; in some such embodiments, an actual process water is used. In other embodiments, a simulated pygas is formed and water is added to the simulated pygas for the determination. For purposes of providing measurements related to the disclosures herein, a simulated pygas consisting essentially of a mixture of toluene, styrene, cyclohexane, n-hexane, and dicyclopentadiene is employed. Partition coefficient is determined by mixing equal volumes of deionized water and simulated pygas, then adding a potential polymerization inhibitor at a concentration range of about 0.1 wt % to 5 wt %, in some embodiments, followed by a period of vigorous mixing, then a period of standing undisturbed to allow the phases to separate; the relative concentration of a species in each phase determines the partition coefficient. For purposes of partition coefficients recited herein, the test is conducted at a target inhibitor concentration of 1 wt % (10,000 ppm) followed by vigorous mixing for 30 minutes, followed by allowing the mixture to stand substantially unperturbed for 30 minutes. The pygas and aqueous phases that result in the unperturbed mixture are separated and concentration of the potential polymerization inhibitor in each phase is quantified, for example by high performance liquid chromatography coupled with mass spectrometry analysis (HPLC-MS). The partition ratio, or partition coefficient, of the potential polymerization inhibitor between the pygas and aqueous phases is then calculated according to the formula $$P = \frac{[I]_{pygas}}{[I]_{aqueoous}}$$

where P is the partition coefficient, $[I]_{pygas}$ is the concentration of the potential polymerization inhibitor in the pygas phase, and $[I]_{aqueous}$ is the concentration of potential polymerization inhibitor in the aqueous phase.

It is understood by those of skill that pygas-water emulsions have variable composition based on feedstock applied to the process as well as the specific process conditions employed in the applicable industrial processes. The concentration and identity of polymerizable species, such as styrene and polymerizable oligomers thereof, in such emulsions is therefore also variable. Further, pygas-water emulsions that exist in process water streams can include variable concentrations of polymerizable species partitioned between the two phases (pygas and water). Such variable conditions can arise, for example, where one or more additional compounds present in the process water stream acts as a cosolvent, hydrotrope, or the like, leading to variable partitioning of polymerizable species between the phases. It is therefore advantageous where possible to determine the pygas-water partition coefficient of a polymerization inhibitor in a pygas-water combination wherein the pygas, the water, or both are obtained from a water recycling loop. Most advantageously, the pygas so obtained is taken from the same water recycling loop into which the first and second polymerization inhibitors will be applied. Using actual samples of process water to determine pygas-water partitioning provides an optimal measurement applicable to the individual system, process conditions, and feedstock employed in the industrial pyrolysis process.

We have found that addition to a process water of a first polymerization inhibitor having a pygas-water partition coefficient of less than 9 and greater than zero is advantageous to inhibit polymerization of polymerizable species that are present in an aqueous phase of the process water, while addition to a process water of a second polymerization inhibitor having a pygas-water partition coefficient of greater than 1000 and as high as 50,000 is advantageous to inhibit polymerization of polymerizable species that are present in a pygas phase of the process water. In embodiments, the molar ratio of the first polymerization inhibitor to the second polymerization inhibitor applied to the process water is generally about 1:9 to 9:1, or about 1:8 to 9:1, or about 1:7 to 9:1, or about 1:6 to 9:1, or about 1:5 to 9:1, or about 1:4 to 9:1, or about 1:3 to 9:1, or about 1:2 to 9:1, or about 1:1 to 9:1, or about 1:9 to 8:1, or about 1:9 to 7:1, or about 1:9 to 6:1, or about 1:9 to 5:1, or about 1:9 to 4:1, or about 1:9 to 3:1, or about 1:9 to 2:1, or about 1:9 to 1:1, or about 1:8 to 8:1, or about 1:7 to 7:1, or about 1:6 to 6:1, or about 1:5 to 5:1, or about 1:4 to 4:1, or about 1:3 to 3:1, or about 1:2 to 2:1, or about 1:1. In embodiments, the weight ratio of the first polymerization inhibitor to the second polymerization inhibitor applied to the process water is generally about 1:9 to 9:1, or about 1:8 to 9:1, or about 1:7 to 9:1, or about 1:6 to 9:1, or about 1:5 to 9:1, or about 1:4 to 9:1, or about 1:3 to 9:1, or about 1:2 to 9:1, or about 1:1 to 9:1, or about 1:9 to 8:1, or about 1:9 to 7:1, or about 1:9 to 6:1, or about 1:9 to 5:1, or about 1:9 to 4:1, or about 1:9 to 3:1, or about 1:9 to 2:1, or about 1:9 to 1:1, or about 1:8 to 8:1, or about 1:7 to 7:1, or about 1:6 to 6:1, or about 1:5 to 5:1, or about 1:4 to 4:1, or about 1:3 to 3:1, or about 1:2 to 2:1, or about 1:1.

The ratios above are variable depending on the pygas-water partition coefficient of the first and the second polymerization inhibitors. That is, the relative ratio of the two inhibitors is adjusted to provide an effective concentration of each of the first and second polymerization inhibitor in a treated process water, wherein the effective amount applied is determined by measuring the pygas-water partition coefficient and supplying at least 0.5 ppm of a polymerization inhibitor to each of the pygas and water phases present in the water recycling loop. Thus, in a method of the invention, the pygas-water partition coefficient is determined for both the first polymerization inhibitor and the second polymerization inhibitor, employing a pygas-water mixture (simulated or actual) to determine the pygas-water partition coefficient. The amount of each polymerization inhibitor is then adjusted so that there is at least 0.5 ppm polymerization inhibitor in each of the pygas and water phases within the water recycling loop. In some embodiments, one or both polymerization inhibitors are present in both phases; the methods of the invention provide the operator with means to effectively inhibit polymerization in both the pygas and water phases, presenting a total solution to a previously unarticulated problem associated with polymerization within process waters: namely, the location of polymerization reactions can occur in both the water phase and in the pygas phase.

The total concentration of the first polymerization inhibitor plus the second polymerization inhibitor applied to a water recycling loop of an industrial processing system is about 5 ppm to 500 ppm based on the weight of the process water, or about 5 ppm to 400 ppm, or about 5 ppm to 300 ppm, or about 5 ppm to 200 ppm, or about 5 ppm to 100 ppm, or about 10 ppm to 500 ppm, or about 10 ppm to 400 ppm, or about 10 ppm to 300 ppm, or about 10 ppm to 200 ppm, or about 10 ppm to 100 ppm based on the weight of the process water to be addressed using the methods of the invention.

The first polymerization inhibitor is a polymerization inhibitor having a pygas-water partition coefficient of greater than zero and less than 9. Exemplary but non-limiting examples of first polymerization inhibitors include 2,2,6,6-tetramethylpiperidinyl-1-oxyl (TEMPO), 1-hydroxy-2,2,6,6-tetramethylpiperidine (TEMPOH), 4-hydroxy-2,2,6,6-tetramethylpiperidinyl-1-oxyl (HTMPO), 4-oxo-2,2,6,6-tetramethylpiperidinyl-1-oxyl (OTEMPO), 1,4-dihydroxy-2,2,6,6-tetramethylpiperidine (HTMPOH), and 1-hydroxy-4-oxo-2,2,6,6-tetramethylpiperidine (OTEMPOH). In some embodiments, the first polymerization inhibitor is a mixture of two or more compounds, wherein each such compound is a polymerization inhibitor and has a pygas-water partition coefficient of greater than zero and less than 9, or alternatively wherein the average of the partition coefficients of the two or more first polymerization inhibitors is greater than zero and less than about 9. In embodiments, a first polymerization inhibitor has a pygas-water partition coefficient of about 0.0001 to 9, or about 0.001 to 9, or about 0.01 to 9, or about 0.1 to 9, or about 0.0001 to 8, or about 0.0001 to 7, or about 0.0001 to 6, or about 0.0001 to 5, or about 0.0001 to 4, or about 0.0001 to 3, or about 0.0001 to 2, or about 0.0001 to 1, or about 0.001 to 1, or about 0.01 to 1, or about 0.01 to 0.9, or about 0.01 to 0.8, or about 0.01 to 0.7, or about 0.01 to 0.6, or about 0.01 to 0.5, or about 0.01 to 0.4, or about 0.01 to 0.3, or about 0.01 to 0.2, or about 0.01 to 0.1.

The second polymerization inhibitor is a polymerization inhibitor having a pygas-water partition coefficient of greater than 1000 and less than 50,000. Exemplary but non-limiting examples of second polymerization inhibitors include 1,4-phenylenediamine (PDA) and alkylated derivatives thereof such as N,N'-di-sec-butyl-1,4-phenylenediamine (sBuPDA). In some embodiments, the second polymerization inhibitor is a blend of two or more compounds, wherein each compound is a polymerization inhibitor and has a pygas-water partition coefficient of greater than 1000 and less than 50,000. In embodiments, a second polymerization inhibitor has a pygas-water partition coefficient of about 1000 to 45,000, or about 1000 to 40,000, or about 1000 to 35,000, or about 1000 to 30,000, or about 1000 to 25,000, or about 1000 to 20,000, or about 1000 to 15,000, or about 1000 to 10,000, or about 2000 to 50,000, or about 3000 to 50,000, or about 4000 to 50,000, or about 5000 to 50,000, or about 6000 to 50,000, or about 7000 to 50,000, or about 8000 to 50,000, or about 9000 to 50,000, or about 10,000 to 50,000, or about 2000 to 20,000, or about 5000 to 25,000, or about 5000 to 20,000, or about 5000 to 15,000.

We have found that by applying both a first polymerization inhibitor and a second polymerization inhibitor to a pyrolysis process water in a molar ratio of about 1:9 to 9:1 or in some embodiments in a weight ratio of about 1:9 to 9:1, superior results are obtained in reduction of fouling of equipment contacted with the treated process water relative to untreated process water and use of the second polymerization inhibitor alone.

Methods of Reducing Fouling

According to the methods of the invention, a first polymerization inhibitor and second polymerization inhibitor are applied to a process water within a water recycling loop of an industrial processing system such as a pyrolysis system. The first and second polymerization inhibitors are usefully added to the water recycling loop at any location within the loop, as will be appreciated by those of skill. The first and second polymerization inhibitors may be added serially or contemporaneously. In some embodiments, first polymerization inhibitor, second polymerization inhibitor, or both are employed neat or mixed with a solvent and optionally other additive compounds, then injected into the water recycling loop at a selected location. In some embodiments, one or both of the first and second polymerization inhibitors are advantageously added to the process water stripper (PWS), downstream of the quench water tower (QWT) of a pyrolysis plant, where pyrolysis byproducts are initially condensed upon contacting the hot pyrolysis gases with the quench water and further downstream from the quench water separator (QWS) that provides bulk separation of pygas and water phases. It is well known by those of skill that the QWS does not completely resolve the phases and that pyrolysis byproducts and pygas byproducts, including polymerizable species, remain entrained within the water phase as dispersed or emulsified. Thus, the water phase having entrained pyrolysis byproducts and pygas byproducts is applied to the PWS. We have found that adding the first and second polymerization inhibitors in the PWS reduces or even prevents fouling of the surfaces subsequently contacted by the water carrying the pyrolysis byproducts and pygas byproducts along the water recycling loop of the pyrolysis plant. However, adding the first, second, or both first and second polymerization inhibitors at another location is preferable in some embodiments for reasons of system design or process details.

One or more additional components are optionally added to the water recycling loop along with one or both of the first and second polymerization inhibitors. The one or more additional components include water soluble or miscible solvents such as $C_1$-$C_6$ alcohols, glycerol, $C_1$-$C_8$ glycols such as ethylene glycol, propylene glycol, diethylene glycol, and triethylene glycol, ethers of such glycols such as diethylene glycol monobutyl ether, $C_1$-$C_4$ ketones and aldehydes, and the like; and mixtures of two or more thereof. In some embodiments, the one or more additional components include hydrophobic solvents such as such as aromatic solvents, paraffinic solvents, or mixtures of both. Examples of suitable hydrophobic solvents include heavy aromatic naphtha, toluene, ethylbenzene, and isomeric hexanes, and mixtures of two or more thereof. In some embodiments, a mixture of one or more water soluble or miscible solvents and one or more hydrophobic solvents are additional components added to the water recycling loop along with one or both of the first and second polymerization inhibitors.

In some embodiments, the first polymerization inhibitor, the second polymerization inhibitor, or both are applied to a water recycling loop in the absence of a solvent. In other embodiments, a dispersion, emulsion, or solution of the first polymerization inhibitor, the second polymerization inhibitor, or a blend of the first and second polymerization inhibitor is applied to the recycling water loop. A dispersion, emulsion, or solution is formed by addition of at least one solvent to the first polymerization inhibitor, the second polymerization inhibitor, or a blend of thereof.

The first polymerization inhibitor, the second polymerization inhibitor, or a blend of the first and second polymerization inhibitor is easily added at any point within the water recycling loop to provide antifouling properties to the treated process water formed therein. In some embodiments, the first polymerization inhibitor and the second polymerization inhibitor are applied to the water recycling loop downstream from one or more coalescing units. In some embodiments, the first polymerization inhibitor and the second polymerization inhibitor are applied to the quench water tower (QWT). In some such embodiments, the concentration of the first polymerization inhibitor and the second polymerization inhibitor in the process water is measured as an average weight of the inhibitors present in the QWT, and a selected amount of the first and second polymerization inhibitors is applied to the QWT to form a treated process water therein.

The first polymerization inhibitor and second polymerization inhibitor are applied to a water recycling loop to target about 5 ppm to 500 ppm based on the mass flow applied to a dilution steam generator, or about 10 ppm to 500 ppm, or about 20 ppm to 500 ppm, or about 30 ppm to 500 ppm, or about 40 ppm to 500 ppm, or about 50 ppm to 500 ppm, or about 60 ppm to 500 ppm, or about 70 ppm to 500 ppm, or about 80 ppm to 500 ppm, or about 90 ppm to 500 ppm, or about 100 ppm to 500 ppm, or about 5 ppm to 450 ppm, or about 5 ppm to 400 ppm, or about 5 ppm to 350 ppm, or about 5 ppm to 300 ppm, or about 5 ppm to 250 ppm, or about 5 ppm to 200 ppm, or about 5 ppm to 150 ppm, or about 5 ppm to 100 ppm, or about 10 ppm to 300 ppm, or about 10 ppm to 250 ppm, or about 50 ppm to 250 ppm, or about 50 ppm to 200 ppm based on the mass flow applied to the dilution steam generator.

Applying the first and second polymerization inhibitors to the water recycling loop is easily carried out using techniques familiar to those of ordinary skill in the art. For example, one or both of the first and second polymerization initiators are added in solid form to an opening in the water recycling loop. In embodiments, one or both of the first and second polymerization initiator are applied as a solution, emulsion, or dispersion that is sprayed, dripped, or poured into an opening within the water recycling loop.

The presence of at least 5 ppm total of the first and second polymerization initiators, present in a weight ratio of about 1:9 to 9:1 within the process water of a water recycling loop of an ethylene plant reduces or prevents the fouling of surfaces contacting process water within the water recycling loop. The presence of at least 5 ppm total of the first and second polymerization initiators, present in a molar ratio of about 1:9 to 9:1 within the process water of a water recycling loop of an ethylene plant reduces or prevents the fouling of surfaces contacting process water within the water recycling loop.

Thus, in some embodiments, a method of treating a process water includes applying to the process water present in an ethylene production plant a first polymerization inhibitor and a second polymerization inhibitor to form a treated process water. In embodiments, the treated process water proceeds downstream from the location of the applying within the water recycling loop.

After the applying of the first and second polymerization inhibitors to the water recycling loop, treated process water is observed to include more pygas than process water obtained without addition of the first and second polymerization inhibitors. This is because polymerized solids cause fouling and concomitant loss of pygas solids from the process water, whereas the treated process water undergoes reduced polymerization and therefore less fouling. Stated differently, less fouling of equipment by precipitation is observed in the treated process water than in process water without addition of the first and second polymerization inhibitors. Fouling in the water recycling loop is evidenced by operational change of pressure ($\Delta P$) in the PWS, and/or heat transfer loss on the DSG reboiler, which necessitates higher heat flow from the heating source or results in a reduced production of dilution steam as fouling occurs.

In embodiments, reduction in fouling is measured as decreased deposition of solids on process equipment contacted with a treated process water compared to deposition of solids on process equipment contacted with the untreated process water over the same time period.

In some embodiments, the treated process water includes about 1% to 25% higher total organic carbon content than a process water wherein first and second polymerization inhibitors were not added to the process water. In some embodiments, a treated process water includes about 1% to 20% higher total organic carbon content than process water collected from a resolved emulsion wherein first and second polymerization inhibitors were not added to the process water, or about 1% to 15% higher, or about 1% to 10% higher, or about 1% to 8% higher, or about 1% to 6% higher, or about 2% to 25% higher, or about 5% to 25% higher, or about 10% to 25% higher total organic carbon content than process water collected from a resolved emulsion wherein first and second polymerization inhibitors were not added to the process water.

The application of the first and second polymerization inhibitors to a process water, even at process water temperatures of about 60° C. to 110° C., or about 70° C. to 110° C., or about 80° C. to 110° C., or about 60° C. to 100° C., or about 60° C. to 90° C. does not lead to foaming, viscosification, or fouling of equipment within the water recycling loop. That is, the treated process water does not exhibit elevated foaming or viscosification in the water recycling loop, and fouling is also reduced or eliminated in the treated process water when compared to untreated process water.

EXPERIMENTAL

The following examples are intended to show experimental embodiments of the invention. The embodiments are not limiting to the scope of the claims appended hereto. It will be recognized that various modifications and changes may be made without following the experimental embodiments described herein, further without departing from the scope of the claims.

Example 1

The partition ratio of the polymerization inhibitor 1-hydroxy-2,2,6,6-tetramethylpiperidinyl-1-oxyl (HTMPO) between pygas and aqueous phases was determined by the following procedure. HTMPO was added to a mixture of equal volumes of de-ionized water and simulated pyrolysis gasoline (pygas). The simulated pygas consisted of a mixture of toluene, styrene, cyclohexane, n-hexane, and dicyclopentadiene. The amounts of inhibitor and liquid phases used were such that the inhibitor was present at a total concentration of 1.0 wt % based on the weight of the combined phases.

The system consisting of the inhibitor, pygas phase, and aqueous phase was vigorously stirred for thirty minutes, after which time it was allowed to sit undisturbed for an additional thirty minutes. The immiscible pygas and aqueous phases were then separated.

A stock solution of known concentration of HTMPO in acetonitrile was diluted with water/acetonitrile to give five different solutions at concentrations spanning an appropriate working range of a high performance liquid chromatograph (HPLC) coupled to a mass spectrometer with an electrospray ionization (ESI) source. The five dilute solutions were analyzed as standards using HPLC-MS, and the areas of the peaks corresponding to HTMPO in these solutions were used to construct a calibration curve of peak area vs. concentration (mass fraction, ppm).

The pygas phase of unknown concentration of HTMPO, separated from the aqueous phase in the first part of the experiment, was diluted with water/acetonitrile to give a solution whose concentration was within the range of the calibration curve. The dilute pygas solution was analyzed by HPLC-MS, and the concentration of HTMPO in this pygas solution was calculated by interpolation of its HTMPO peak area into the calibration curve. The concentration of HTMPO in the original, undiluted pygas phase was calculated by applying the dilution factor to the interpolated concentration of the diluted solution. The measurement and calculation was conducted a total of three times on the pygas phase. The concentration of HTMPO in the aqueous phase separated in the first part of the experiment was determined in the same manner as that of the pygas phase.

The partition coefficient of HTMPO between the pygas and aqueous phases was calculated according to the formula $$P = \frac{[HTMPO]_{pygas}}{[HTMPO]_{aqueous}},$$

where P is the partition coefficient, $[HTMPO]_{pygas}$ is the concentration of HTMPO in the pygas phase, and $[HTMPO]_{aqueous}$ is the concentration of HTMPO in the aqueous phase. Table 1 summarizes data collected during the determination of the partition coefficient for HTMPO.

TABLE 1

Concentration and partition coefficient data for HTMPO

| Trial | [HTMPO] (ppm) in Undiluted Phase |
|---|---|
| Pygas Phase | |
| 1 | 597.8 |
| 2 | 530.2 |
| 3 | 620.5 |
| Average[a] | 582.8 ± 47.0 |
| Aqueous Phase | |
| 1 | 7155.2 |
| 2 | 7142.9 |
| 3 | 7934.4 |
| Average[a] | 7410.8 ± 453.5 |
| Partition Ratio[a] | 0.079 ± 0.008 |

[a]Standard uncertainty is given.

Example 2

The partition coefficient of the polymerization inhibitor 1,4-dihydroxy-2,2,6,6-tetramethylpiperidine (HTMPOH) between pygas and aqueous phases was determined by the same procedure used in Example 1, except that HTMPOH was used in place of HTMPO. Table 2 summarizes data collected during the determination of the partition coefficient for HTMPOH.

TABLE 2

Concentration and partition coefficient data for HTMPOH.

| Trial | [HTMPOH] (ppm) in Undiluted Phase |
|---|---|
| Pygas Phase | |
| 1 | 27.8 |
| 2 | 26.6 |
| 3 | 27.2 |
| Average[a] | 27.2 ± 0.6 |
| Aqueous Phase | |
| 1 | 2807.5 |
| 2 | 2764.3 |
| 3 | 2917.6 |
| Average[a] | 2829.8 ± 79.0 |
| Partition Ratio[a] | 0.0096 ± 0.0003 |

[a]Standard uncertainty is given.

Example 3

The partition coefficient of the polymerization inhibitor N,N'-di-sec-butyl-1,4-phenylenediamine (sBuPDA) between pygas and aqueous phases was determined by the same procedure used in Experiment A, except that sBuPDA was used in place of HTMPO. Table 3 summarizes data collected during the determination of the partition coefficient for sBuPDA.

TABLE 3

Concentration and partition coefficient data for sBuPDA

| Trial | [sBuPDA] (ppm) in Undiluted Phase |
|---|---|
| Pygas Phase | |
| 1 | 4218.2 |
| 2 | 4109.2 |
| 3 | 3900.2 |
| Average[a] | 4075 ± 161.6 |
| Aqueous Phase | |
| 1 | 0.29 |
| 2 | 0.26 |
| 3 | 0.32 |
| Average[a] | 0.29 ± 0.03 |
| Partition Ratio[a] | 14000 ± 2000 |

[a]Standard uncertainty is given.

Example 4

Using an alumina column, 4-tert-butylcatechol (TBC) was removed from styrene. Freshly de-inhibited styrene (9 mL) was charged into each of twenty-four Ace Glass #15 threaded pressure tubes equipped with PTFE screw caps and fluoroelastomer (FETFE) O-rings. Dissolved oxygen was purged out of the solutions by sparging with nitrogen for 2 minutes. Immediately after that, the tubes were capped under a nitrogen headspace. Polymerization reactions were carried out by loading the tubes into a heating block that had been preheated to 122° C. After 30 minutes, and every 15 minutes after that, four tubes were retrieved from the block and the polymerization reaction quenched by cooling in an ice bath. The amount of polymer formed was determined by precipitation with methanol according to the ASTM D2121 method.

A solution consisting of 0.33 mmolal of the inhibitor to be tested and inhibitor-free styrene was prepared. Portions of 9 mL were charged into the reactor tubes. The procedure above was used to remove oxygen, polymerize the solutions, and measure the amount of polymer formed.

Figure 1:
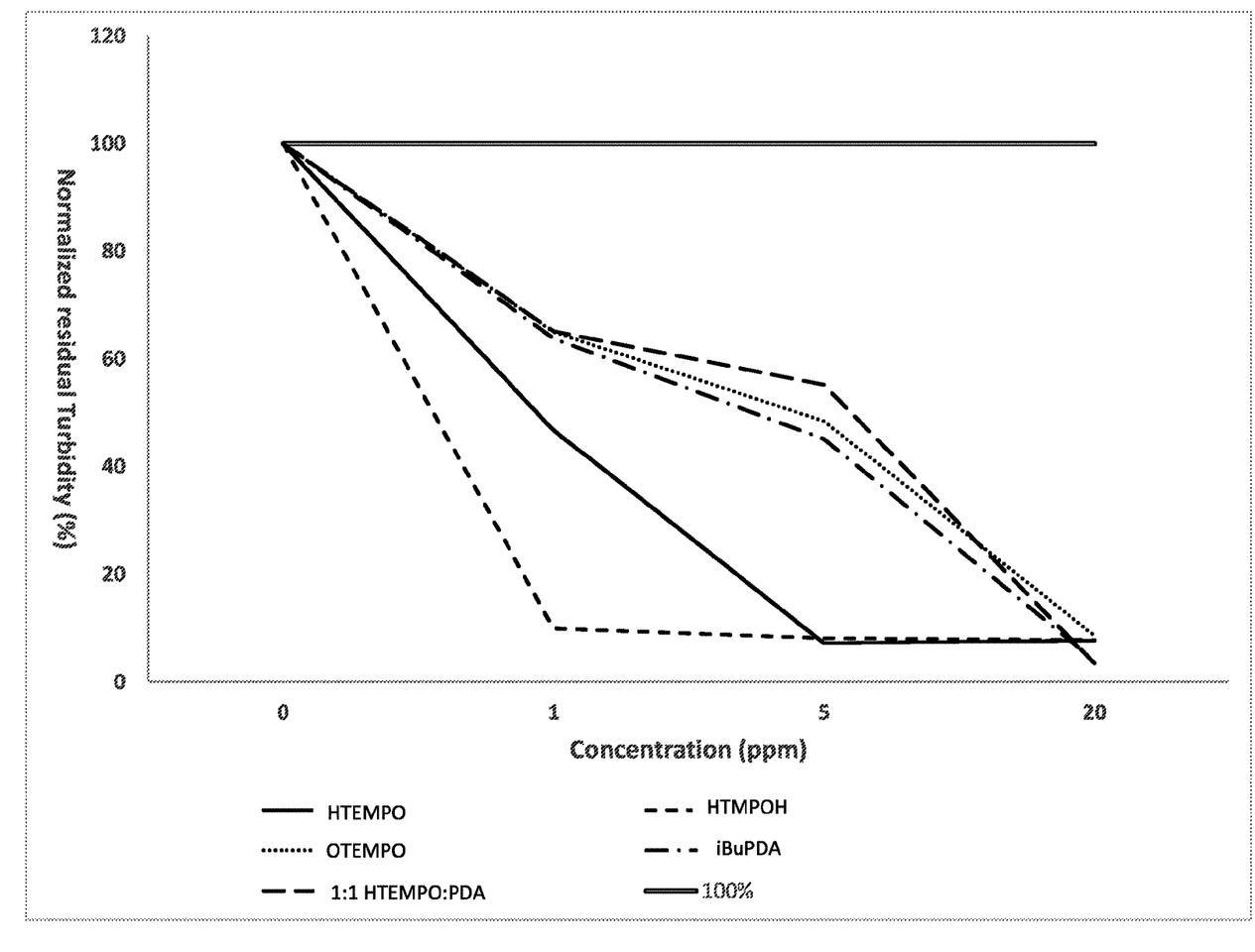
FIG. 1 is a plot comparing the results of turbidity testing of the aqueous phase of a water-pygas system in the presence of various polymerization inhibitors.

The polymerization inhibition tests were carried out by introducing water and gasoline representative of the process to four vessels. The first vessel was a control experiment while in the remaining vessels varying dosages and combinations of inhibitors were introduced. The vessels were stirred vigorously for five minutes and then allowed to stand without disturbance for four hours. The turbidity of each water phase was then measured. Results of turbidity testing with individual polymerization inhibitors and a 50:50 wt:wt mixture of HTMPO and 1,4-phenylene diamine in various total amounts are shown in FIG. 1.

The greater the production of polymer in the water phase, the greater the turbidity of the tested systems after five minutes of mixing and four hours of polymerization time. The reduced turbidity of the systems containing the inhibitor as compared to a blank solution indicates that the polymerization inhibitors effectively reduced polymerization.

The invention illustratively disclosed herein can be suitably practiced in the absence of any element which is not specifically disclosed herein. Additionally each and every embodiment of the invention, as described herein, is intended to be used either alone or in combination with any other embodiment described herein as well as modifications, equivalents, and alternatives thereof. In various embodiments, the invention suitably comprises, consists essentially of or consists of the elements described herein and claimed according to the claims. It will be recognized that various modifications and changes may be made without following the example embodiments and applications illustrated and described herein, and without departing from the scope of the claims.

What is claimed is:

1. A method of reducing fouling in a water recycling loop, the method comprising:
    selecting a first polymerization inhibitor having a a pygas-water partition coefficient of about 0.0001 to 9 and a second polymerization inhibitor having a pygas-water partition coefficient of about 1000 to 50,000, wherein the pygas-water partition coefficient is determined in water and either a pygas obtained from a process water or a simulated pygas comprising toluene, styrene, cyclohexane, n-hexane, and dicyclopentadiene;
    applying the first polymerization inhibitor and the second polymerization inhibitor to a process water within the water recycling loop to form a treated process water, wherein the total concentration of the first and second polymerization inhibitors in the treated process water is about 5 ppm to 500 ppm; and
    contacting the treated process water with an interior surface of the water recycling loop.

2. The method of claim 1 wherein the total concentration of the first and second polymerization inhibitors in the treated process water is about 10 ppm to 100 ppm.

3. The method of claim 1 wherein the first and second polymerization inhibitors are applied to the process water at a weight ratio of about 1:9 to 9:1.

4. The method of claim 1 wherein the first polymerization inhibitor has a pygas-water partition coefficient of about 0.001 to 1.

5. The method of claim 1 wherein the first polymerization inhibitor is selected from 2,2,6,6-tetramethylpiperidinyl-1-oxyl, 1-hydroxy-2,2,6,6-tetramethylpiperidine, 4-hydroxy-2,2,6,6-tetramethylpiperidinyl-1-oxyl, 4-oxo-2,2,6,6-tetramethylpiperidinyl-1-oxyl, 1,4-dihydroxy-2,2,6,6-tetramethylpiperidine, and 1-hydroxy-4-oxo-2,2,6,6-tetramethylpiperidine, or a combination thereof.

6. The method of claim 1 wherein the second polymerization inhibitor has a pygas-water partition coefficient of about 5000 to 25,000.

7. The method of claim 1 wherein the second polymerization inhibitor is selected from 1,4-phenylenediamine, alkylated derivatives thereof, or a blend thereof.

8. The method of claim 1 wherein the applying is downstream from a coalescer in a pyrolysis plant.

9. The method of claim 1 wherein the process water and/or the treated process water is present at a temperature of about 60° C. to 110° C.

10. The method of claim 1 wherein the water recycling loop comprises a dilution steam system.

* * * * *